(12) United States Patent
Feloney

(10) Patent No.: US 8,998,883 B1
(45) Date of Patent: Apr. 7, 2015

(54) FEMALE URETHRAL CATHETERIZATION ASSISTING DEVICE

(71) Applicant: Michael Feloney, Omaha, NE (US)

(72) Inventor: Michael Feloney, Omaha, NE (US)

( * ) Notice: Subject to any disclaimer, the term of this patent is extended or adjusted under 35 U.S.C. 154(b) by 24 days.

(21) Appl. No.: 13/845,947

(22) Filed: Mar. 18, 2013

Related U.S. Application Data

(63) Continuation-in-part of application No. 12/875,577, filed on Sep. 3, 2010.

(51) Int. Cl.
| | | |
|---|---|---|
| *A61M 25/01* | (2006.01) | |
| *A61M 25/02* | (2006.01) | |
| *A61M 25/08* | (2006.01) | |
| *A61M 25/00* | (2006.01) | |
| *A61B 17/29* | (2006.01) | |

(52) U.S. Cl.
CPC ........... *A61M 25/02* (2013.01); *A61M 25/0017* (2013.01); *A61B 2017/2936* (2013.01); *A61M 25/002* (2013.01); *A61B 2017/2916* (2013.01); *A61M 25/0111* (2013.01); *A61B 2017/2934* (2013.01); *A61M 25/01* (2013.01); *A61M 25/0113* (2013.01); *A61B 2017/2945* (2013.01); *A61M 25/0041* (2013.01); *A61M 25/0068* (2013.01); *A61B 2017/2915* (2013.01); *A61M 2209/08* (2013.01); *A61M 2025/0191* (2013.01); *A61M 2210/1078* (2013.01); *A61M 2210/1089* (2013.01); *A61M 2202/0496* (2013.01)

(58) Field of Classification Search
CPC ................. A61M 2025/02; A61M 2025/0105; A61M 2025/0177; A61M 2025/0191; A61M 2025/0206; A61M 2025/0253; A61M 2025/026; A61M 2025/028; A61M 2202/0496; A61M 2209/08; A61M 2209/082; A61M 2209/084; A61M 2209/086; A61M 2209/088; A61M 2210/1078; A61M 2210/1089; A61M 2210/1092; A61M 25/0017; A61M 25/002; A61M 25/0021; A61M 25/0041; A61M 25/0068; A61M 25/008; A61M 25/0082; A61M 25/0097; A61M 25/01; A61M 25/0105; A61M 25/0111; A61M 25/0113; A61M 25/013; A61M 25/0136; A61M 25/02; A61B 2017/2915; A61B 2017/2916; A61B 2017/2917; A61B 2017/2934; A61B 2017/2936; A61B 2017/2937; A61B 2017/2945
USPC .................................. 294/170, 171, 191, 174
See application file for complete search history.

(56) References Cited

U.S. PATENT DOCUMENTS

| | | | |
|---|---|---|---|
| 3,867,945 | A | 2/1975 | Long |
| 3,908,637 | A | 9/1975 | Doroshow |
| 3,920,023 | A | 11/1975 | Dye et al. |
| 4,790,810 | A | 12/1988 | Pugh et al. |
| 4,986,823 | A * | 1/1991 | Anderson et al. .............. 604/329 |
| 4,995,872 | A * | 2/1991 | Ferrara ......................... 604/523 |
| 5,045,078 | A * | 9/1991 | Asta .............................. 604/329 |
| 5,116,309 | A | 5/1992 | Coll |
| 5,152,749 | A | 10/1992 | Giesy et al. |
| 5,334,185 | A | 8/1994 | Giesy et al. |
| 5,356,382 | A | 10/1994 | Picha et al. |
| 5,454,798 | A | 10/1995 | Kubalak et al. |
| 5,472,435 | A | 12/1995 | Sutton |

(Continued)

*Primary Examiner* — Adam Marcetich
(74) *Attorney, Agent, or Firm* — Suiter Swantz pc llo

(57) ABSTRACT

A female urethral catheterization assisting device may include a handle, an elongated shaft and a catheter holding mechanism. The catheter holding mechanism may hold a catheter securely so that a patient may position, orient and insert a catheter into the patient's urethra. The handle and elongated shaft assist in positioning, orienting and inserting the catheter by extending the patient's reach.

10 Claims, 5 Drawing Sheets

(56) References Cited

U.S. PATENT DOCUMENTS

| | | | |
|---|---|---|---|
| 5,582,611 A * | 12/1996 | Tsuruta et al. | 606/46 |
| 5,653,700 A * | 8/1997 | Byrne et al. | 604/329 |
| 5,681,274 A | 10/1997 | Perkins et al. | |
| 5,730,150 A * | 3/1998 | Peppel et al. | 600/585 |
| 5,772,670 A * | 6/1998 | Brosa | 606/108 |
| 6,063,063 A | 5/2000 | Harboe et al. | |
| 6,379,334 B1 | 4/2002 | Frassica | |
| 6,695,831 B1 | 2/2004 | Tsukada et al. | |
| 2002/0002363 A1 | 1/2002 | Urakawa et al. | |
| 2002/0130059 A1 * | 9/2002 | Armijo | 206/438 |
| 2003/0004496 A1 | 1/2003 | Tanghoi | |
| 2003/0135200 A1 | 7/2003 | Byrne | |
| 2005/0070882 A1 | 3/2005 | McBride | |
| 2005/0192560 A1 | 9/2005 | Walls et al. | |
| 2005/0246038 A1 | 11/2005 | O'Keefe et al. | |
| 2006/0025753 A1 | 2/2006 | Kubalak et al. | |
| 2006/0047268 A1 * | 3/2006 | Stephens | 604/533 |
| 2006/0206213 A1 | 9/2006 | Hammond et al. | |
| 2007/0016169 A1 | 1/2007 | Utas et al. | |
| 2007/0288046 A1 * | 12/2007 | Grayzel et al. | 606/174 |
| 2008/0139877 A1 | 6/2008 | Chu et al. | |
| 2008/0275463 A1 | 11/2008 | High | |
| 2009/0088786 A1 * | 4/2009 | Zook et al. | 606/170 |
| 2010/0056910 A1 * | 3/2010 | Yanuma | 600/434 |
| 2010/0213238 A1 * | 8/2010 | Farascioni et al. | 227/176.1 |
| 2010/0256580 A1 * | 10/2010 | Faber | 604/329 |
| 2010/0324540 A1 | 12/2010 | Paulen et al. | |
| 2011/0313361 A1 * | 12/2011 | Shipman | 604/180 |
| 2012/0248170 A1 * | 10/2012 | Marczyk | 227/175.1 |

* cited by examiner

FEMALE URETHRAL CATHETERIZATION ASSISTING DEVICE

PRIORITY

The present application claims the benefit under 35 U.S.C. §120 as a continuation of U.S. application Ser. No. 12/875,577, filed Sep. 3, 2010, which is incorporated herein by reference.

FIELD OF THE INVENTION

The present disclosure relates generally to the field of personal medical devices, and more particularly to a device for assisting urethral catheterization.

BACKGROUND OF THE INVENTION

In urinary catheterization, a latex, polyurethane, or silicone tube known as a urinary catheter is inserted into a patient's bladder via the urethra. Catheterization allows the patient's urine to drain freely from the bladder. While a clinician, often a nurse, may perform the procedure, self-catheterization is also possible.

Self-catheterization creates a substantial risk of catheter contamination. In females, catheter placement is especially critical because the proximity of the vagina to the urethra increases the risk of contamination. Furthermore, a need for catheterization is often comorbid with conditions that hinder manual dexterity; also, obesity may hinder a patient's ability to reach the urethra. Female catheterization can be particularly troublesome because the urethra meatus may be difficult to access.

The risk of contamination during self-catheterization may be reduced by minimizing the patient's contact with the catheter, and by making it easier for the patient to manipulate the catheter. Consequently, it would be advantageous if an apparatus existed that is suitable for assisting a female to catheterize herself.

SUMMARY OF THE INVENTION

Accordingly, the present invention is directed to a novel method and apparatus for assisting a female to catheterize herself.

On embodiment of the present invention is device for assisting a female in catheterizing herself. The device includes a catheter holding mechanism connected to an elongated shaft with a handle for manipulating the position of a catheter in the catheter holding mechanism. The catheter holding mechanism minimizes the females contact with the catheter during catheterization, and the elongated shaft allows the female to position the catheter more easily as compared to the prior art.

The catheter holding mechanism may define a catheter holding channel to hold a catheter in an orientation appropriate for insertion of a catheter into a urethra of a female patient during self-catheterization. The catheter holding channel may include a contour to bend a catheter in such a way as to ease the expulsion of fluids once the catheter is properly inserted into a female patient's urethra. The catheter holding mechanism may include a securing pin to hold a catheter securely in the catheter holding channel.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles.

BRIEF DESCRIPTION OF THE DRAWINGS

The numerous objects and advantages of the present invention may be better understood by those skilled in the art by reference to the accompanying figures in which.

DETAILED DESCRIPTION OF THE INVENTION

Reference will now be made in detail to the subject matter disclosed, which is illustrated in the accompanying drawings. The scope of the invention is limited only by the claims; numerous alternatives, modifications and equivalents are encompassed. For the purpose of clarity, technical material that is known in the technical fields related to the embodiments has not been described in detail to avoid unnecessarily obscuring the description.

The present invention teaches a urethral catheterization assisting device which may be particularly suited for females. Female catheterization may be particularly troublesome because the urethra meatus may be difficult to access. Furthermore, the catheter may be inserted into the vaginal opening by mistake due to the proximity of the urethra to the vaginal opening. If the catheter is inserted into the vagina and then taken out and inserted into the urethra, contaminants may be introduced into the urethra leading to infections. U.S. patent application Ser. No. 12/378,266 filed on Feb. 11, 2009 "Vaginal Barrier and Female Urethral Catheterization Assisting Device" discloses a device for assisting with the troublesome nature of female catheterization.

It is contemplated that the present disclosure may be used in conjunction with U.S. patent application Ser. No. 12/378,266 "Vaginal Barrier and Female Urethral Catheterization Assisting Device" to allow a patient to self-catheterize herself using one hand.

Figure 1:
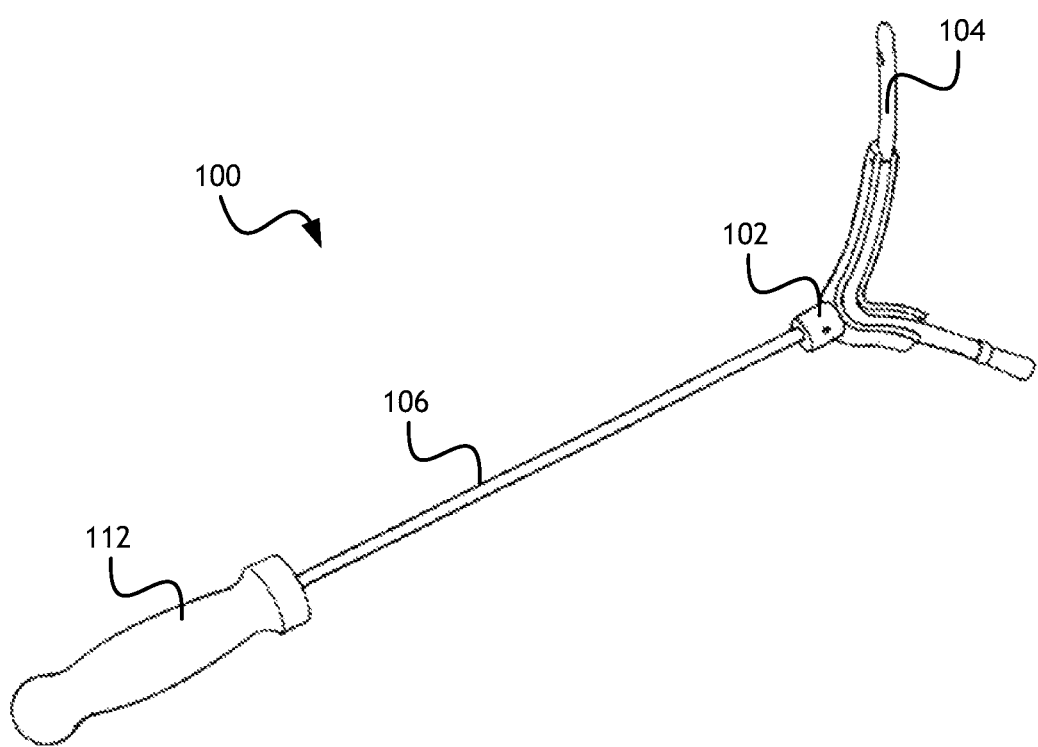
FIG. 1 shows a perspective view of a female urethral catheterization assisting device with a catheter.

Referring to FIG. 1, a perspective view of a female urethral catheterization assisting device (assisting device) 100 with a catheter is shown. The assisting device 100 may include a handle 112 connected to an elongated shaft 106. The elongated shaft 106 may be connected to a catheter holding mechanism 102. The catheter holding mechanism 102 may securely hold a catheter 104 such that a female patient may manipulate the handle 112 of the assisting device 100, and thereby manipulate the position and orientation of the catheter holding mechanism 102, to position the catheter 104 for insertion into the female patient's urethra. The assisting device 100 may be especially useful for female patients with physical limitations affecting reach or manual dexterity.

Figure 2:
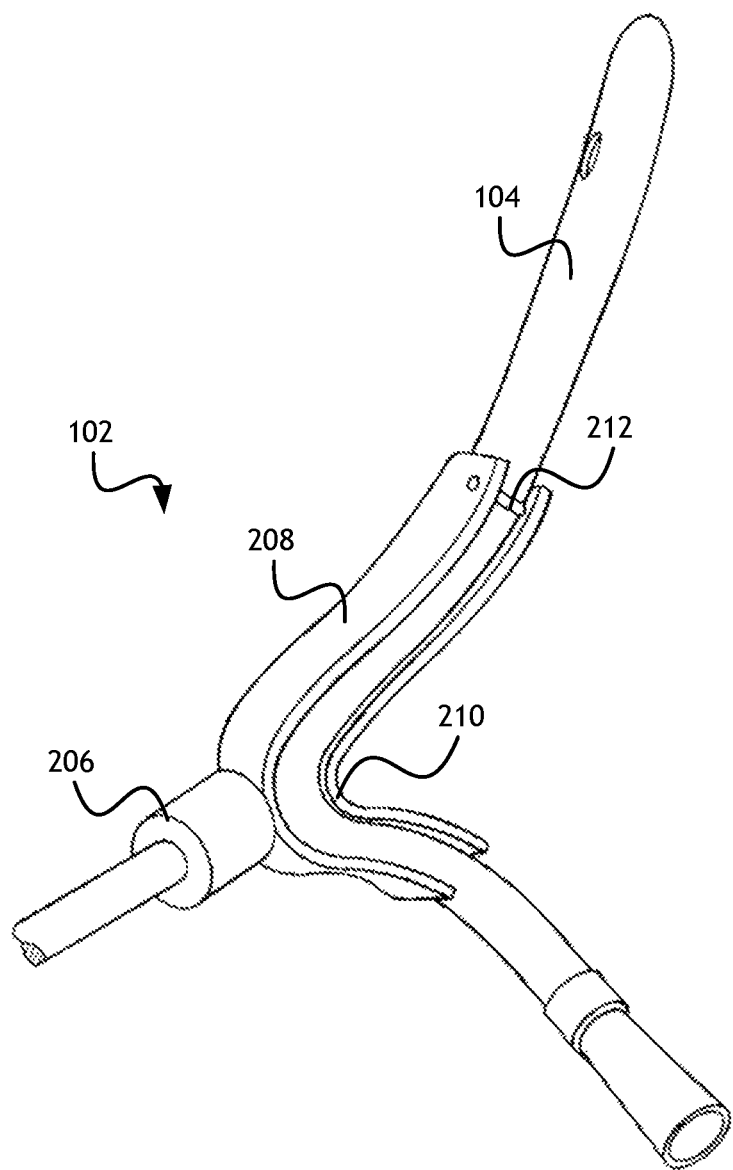
FIG. 2 shows a detail perspective view of a catheter holding mechanism with a catheter.

Referring to FIG. 2, a detail perspective view of a catheter holding mechanism 102 with a catheter 104 is shown. The catheter holding mechanism 102 may connect to an elongated shaft through a shaft connecting element 206. The shaft connecting element 206 may be connected to a catheter holding body 208. The catheter holding body 208 may hold a catheter 104 such that the end of the catheter 104 intended for insertion into a female patient's urethra protrudes sufficiently from the end of the catheter holding body 208 to allow a female patient manipulating an elongated shaft connected to the catheter holding mechanism 102 to insert the catheter 104 into her urethra. The catheter holding body 208 may be made of any material suitable for securely holding a catheter 104 during insertion into a urethra, including but not limited to vinyl, plastic, rubber, latex, Teflon, metal or silicone.

Catheters 104 are intended to be disposable while the catheter holding mechanism is intended to be reusable. The catheter holding mechanism 102 and catheter holding body 208 must therefore hold a catheter 104 securely for insertion into a urethra, but also release the catheter 104 for disposal. A catheter securing pin 212 may hold a catheter 104 in securely within the catheter holding body 208 during insertion. The catheter securing pin 212 may be removed or otherwise disengaged to allow for disposal of the catheter 104.

Catheters 104 used with embodiments of the present invention drain fluid from a patient's bladder (generally urine). It may be advantageous to orient the catheter 104 so as to direct the fluid. The catheter holding body 208 may therefore include a catheter positioning curve 210 to orient the catheter 104 such that when the catheter 104 is inserted into a patient's urethra, the catheter 104 directs fluid in a desirable direction to ease the drainage process.

Figure 3:
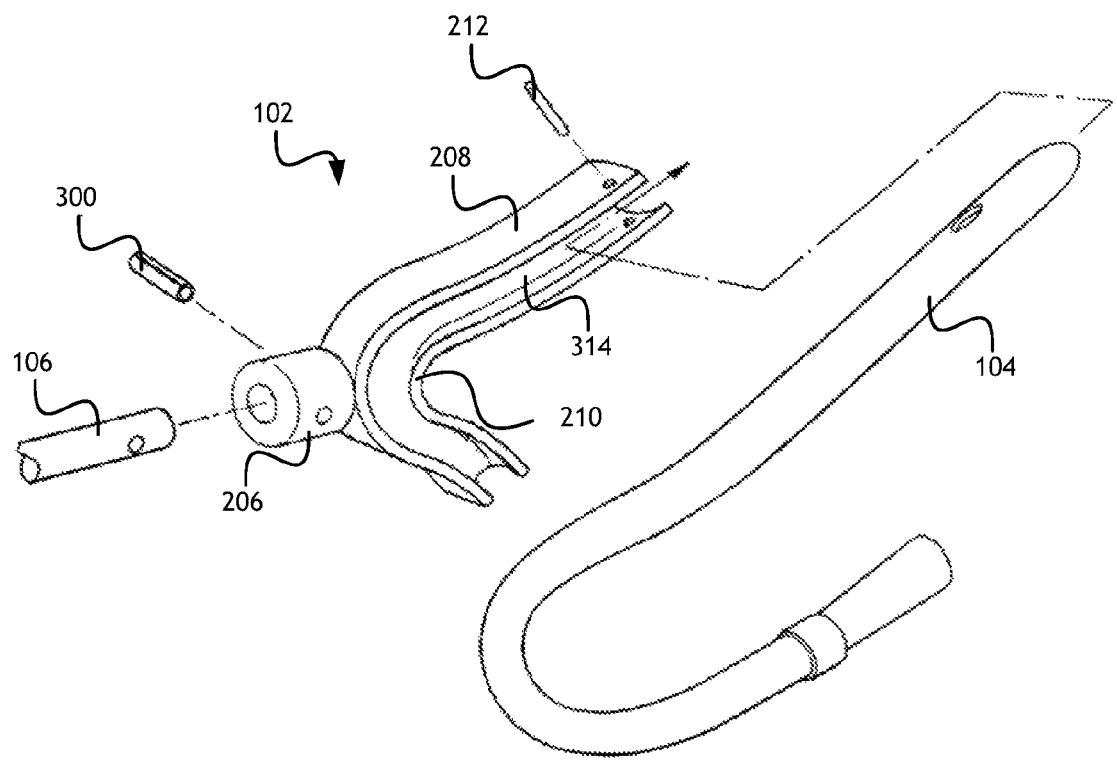
FIG. 3 shows an exploded detail perspective view of a catheter holding mechanism with a catheter.

Referring to FIG. 3, an exploded detail perspective view of a catheter holding mechanism 102 with a catheter 104 is shown. The catheter holding mechanism 102 may be connected to an elongated shaft 106 by a shaft connecting pin 300 inserted through both the elongated shaft 106 and the shaft connecting element 206. Alternatively, the elongated shaft 106 may be permanently connected to the shaft connecting element 206.

The catheter holding mechanism 102 may include a catheter holding body 208. The catheter holding body may define a catheter holding channel 314 to securely hold, direct and orient a catheter 104 during insertion into a urethra. The catheter holding channel 314 may include a catheter positioning curve 210 to orient the catheter 104 such that when the catheter 104 is inserted into a patient's urethra, the catheter 104 directs fluid in a desirable direction to ease the drainage process.

Catheters 104 must be rigid enough, or include components rigid enough to facilitate insertion of the catheter 104 into a urethra. The catheter holding channel 314 may be shaped to accommodate a catheter 104 having a particular rigidity. For example, the catheter holding channel 314 may include one or more ridges that may deform a catheter 104 within operational limits when the catheter 104 is being inserted into the catheter holding channel 314. Such one or more ridges may then serve to hold the catheter 104 within the catheter holding channel 314 during catheter 104 insertion. The catheter positioning curve 210 may also be designed to bend a catheter 104 within operational limits to orient the outflow of fluids. The term "operational limits" in this context should be understood to mean a level of stress that will not cause mechanical failure of the catheter 104.

Figure 4:
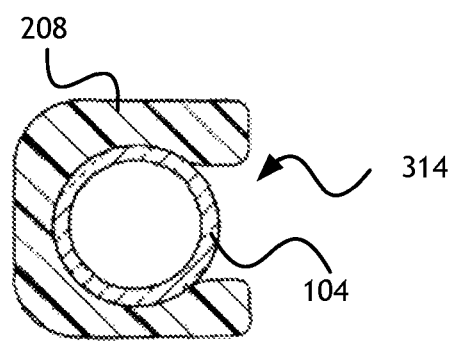
FIG. 4 shows a cross-sectional view of a catheter holding mechanism with a catheter.
Figure 5:
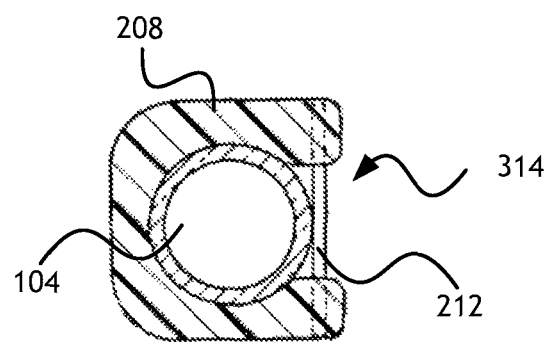
FIG. 5 shows another cross-sectional view of a catheter holding mechanism with a catheter.

Referring to FIG. 4 and FIG. 5, two cross-sectional views of a catheter holding body 208 with a catheter 104 are shown. The catheter holding body 208 may include a catheter holding channel 314. The catheter holding channel 314 may hold a catheter 104 securely for positioning, orienting and insertion into a urethra by manipulation of an elongated shaft connected to the catheter holding body 208. The catheter holding body 208 may include a catheter securing pin 212 to hold the catheter 104 in the catheter holding channel 314 during insertion.

Figure 6:
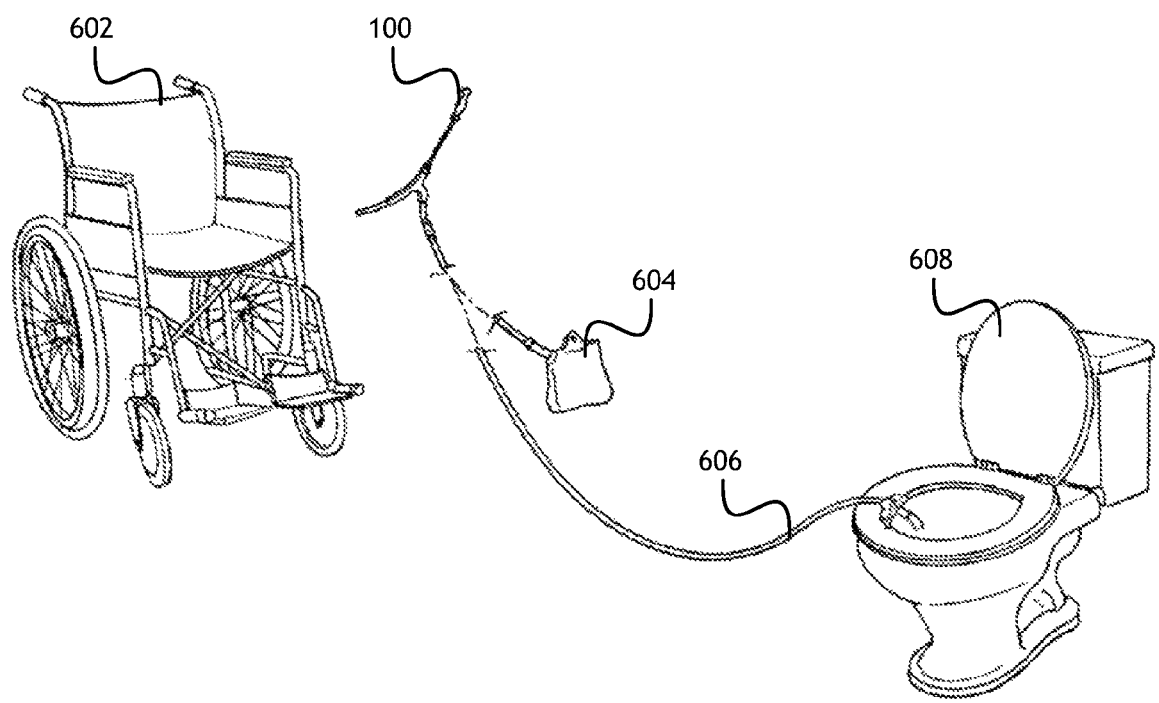
FIG. 6 shows an environmental view of a female urethral catheterization assisting device.

Referring to FIG. 6, an environmental view of an assisting device 100 is shown. The assisting device may be useful for a female patient confined to a wheelchair 602. The patient confined to a wheelchair, and needing catheterization, may use the assisting device 100 to insert a catheter while sitting in the wheelchair 602. The assisting device 100 may position and orient the catheter to allow fluids to drain easily in a desirable direction. For example, the assisting device 100 may direct fluids through the exit portion of the catheter into a collection bag 604. Alternatively, the assisting device 100 may direct fluids through an expulsion tube 606 into a toilet 608.

It is believed that the present invention and many of its attendant advantages will be understood by the foregoing description, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. An apparatus for assisting catheterization, comprising:
    a catheter holding mechanism defining a catheter holding channel configured to hold a catheter;
    an elongated shaft connected to the catheter holding mechanism; and
    a handle connected to the elongated shaft, the handle configured to allow manipulation of a disposable catheter in the catheter holding mechanism through gross motor control,
    a catheter securing pin configured to retain a catheter in the catheter holding channel;
    wherein:
        the catheter holding mechanism is configured to releasably hold a catheter and securely manipulate the orientation of the catheter for insertion into a patient's urethra;
        the catheter holding mechanism comprises a fluid directing curve configured to orient a catheter such that fluid draining through said catheter is directed in a waste fluid receptacle, such fluid directing curve configured to bend a disposable catheter along an arc of at least ninety degrees; and
        the handle and elongated shaft are configured to manipulate the position and orientation of the catheter holding mechanism.

2. The apparatus of claim 1, wherein the catheter holding channel further comprises at least one ridge configured to retain a catheter in the catheter holding channel during a catheter insertion process.

3. The apparatus of claim 1, further comprising a disposable catheter releasably held in the catheter holding mechanism, such catheter configured for insertion into a female urethra.

4. An apparatus for holding a catheter comprising:
    a catheter holding body, such catheter holding body defining a catheter holding channel;
    a catheter securing pin configured to retain a catheter in the catheter holding channel; and
    a shaft connecting element connected to the catheter holding body,
    wherein:

the catheter holding channel is configured to releasably hold a catheter;

the catheter holding channel comprises a fluid directing curve configured to orient a catheter such that fluid draining through said catheter is directed in a waste fluid receptacle, such fluid directing curve configured to bend a disposable catheter along an arc of at least ninety degrees; and the shaft connecting element is configured to translate gross motor movement of an elongated shaft to the catheter holding body and thereby manipulate the position and orientation of the catheter holding body.

5. The apparatus of claim 4, wherein the catheter holding body comprises at least one ridge configured to retain a catheter in the catheter holding channel during a catheter insertion process.

6. The apparatus of claim 4, further comprising a disposable catheter releasably held in the catheter holding channel, such catheter configured for insertion into a female urethra.

7. An apparatus for assisting a female to insert a catheter into her own urethra, comprising:

a holding means for releasably holding a catheter, the holding means comprising a fluid directing curve configured to orient a catheter such that fluid draining through said catheter is directed in a waste fluid receptacle, such fluid directing curve configured to bend a disposable catheter along an arc of at least ninety degrees;

an extending means for manipulating the orientation and position of the holding means at a distance through gross motor movements, such extending means connected to the holding means, the extending means comprising an elongated shaft; and a directing means for applying orienting and positioning forces to the extending means, such directing means, comprising a handle connected to the extending means; and a securing means for retaining a catheter in a catheter holding channel.

8. The apparatus of claim 7, wherein the holding means defines the catheter holding channel configured to hold the catheter.

9. The apparatus of claim 8, wherein the securing means comprises a catheter securing pin.

10. The apparatus of claim 7, further comprising a disposable catheter releasably held in the holding means, such catheter configured for insertion into a female urethra.

* * * * *